US008356180B2

(12) United States Patent
Garcia Morchon et al.

(10) Patent No.: US 8,356,180 B2
(45) Date of Patent: Jan. 15, 2013

(54) MULTIDIMENSIONAL IDENTIFICATION, AUTHENTICATION, AUTHORIZATION AND KEY DISTRIBUTION SYSTEM FOR PATIENT MONITORING

(75) Inventors: Oscar Garcia Morchon, Aachen (DE); Heribert Baldus, Aachen (DE); Axel Gunther Huebner, Munich (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 300 days.

(21) Appl. No.: 12/666,848

(22) PCT Filed: Jul. 1, 2008

(86) PCT No.: PCT/IB2008/052642
§ 371 (c)(1),
(2), (4) Date: Apr. 29, 2010

(87) PCT Pub. No.: WO2009/004578
PCT Pub. Date: Jan. 8, 2009

(65) Prior Publication Data
US 2010/0241862 A1    Sep. 23, 2010

Related U.S. Application Data

(60) Provisional application No. 60/947,789, filed on Jul. 3, 2007, provisional application No. 60/991,901, filed on Dec. 3, 2007.

(51) Int. Cl.
*H04L 9/32* (2006.01)
*H04K 1/00* (2006.01)

(52) U.S. Cl. ........................................ 713/171; 380/270
(58) Field of Classification Search .................. 713/171; 380/270
See application file for complete search history.

(56) References Cited

U.S. PATENT DOCUMENTS

2009/0129599 A1* 5/2009 Garcia et al. .................. 380/279
2009/0205022 A1* 8/2009 Sanchez et al. ................ 726/4

FOREIGN PATENT DOCUMENTS

| WO | 2006051464 A1 | 5/2006 |
| WO | 2006064397 A2 | 6/2006 |
| WO | 2006131849 A2 | 12/2006 |

OTHER PUBLICATIONS

Camtepe, S. A., et al.; Key Distribution Mechanisms for Wireless Sensor Networks: a Survey; 2005; Technical Report, Rensselaer Ploytechnic Institute, Dept. of Computer Science; pp. 1-27.
Sanchez, D., S., et al.; A Deterministic Pairwise Key Pre-distribution Scheme for Mobile Sensor Networks; 2005; First Int'l Conf. on Security and Privacy for Emerging Areas in Communications Networks; pp. 277-288.
Cungang, Y., et al.; Location-based pairwise key establishment and data authentication for wireless sensor networks; 2006; IEEE Information Assurance Workshop; abstract.
Hu, F., et al.; An energy-efficient approach to securing tree-zone-based sensor networks; 2003; IEEE Global Telecommunications Conf.; abstract.

* cited by examiner

*Primary Examiner* — Techane Gergiso

(57) ABSTRACT

A method, wireless system and a wireless device provide multidimensional identification, authentication, authorization and key distribution providing secure communications at a deepest common security domain.

18 Claims, 5 Drawing Sheets

MULTIDIMENSIONAL IDENTIFICATION, AUTHENTICATION, AUTHORIZATION AND KEY DISTRIBUTION SYSTEM FOR PATIENT MONITORING

Monitors and sensors for patients have become ubiquitous and are used to track vital signs and other needed data of patients in both inpatient and outpatient settings. Many known sensors are 'wired' and thus include a wired connection between the sensor and a monitor or other display/data gathering device. As will be appreciated, such wired arrangements can limit free-movement of the patient and thus can be inconvenient. Moreover, limiting a patient's movement can also prevent monitoring of germane patient data outside of sedentary activity and thus may not provide an accurate account of the patient's condition.

The advent of wireless communications has fostered wireless sensors and monitors. In this setting, a set of wireless sensor nodes attached to a patient and measuring patient's vital signs form what is called a body sensor network (BSN). As will be appreciated, sensors can send data garnered from a patient in a wireless manner to a monitor, or to a clinician remotely located from the patient.

Wireless patient monitoring will continue to emerge in application as standards such as IEEE 802.15.4/ZigBee become more prevalent in application. The ZigBee Alliance is defining a Personal Home and Hospital Care (PHHC) profile that describes the use and application of the ZigBee standard to enable secure communications in medical environments and related scenarios to the described in the present patent application.

Such wireless monitoring of patient data in ZigBee-based networks, and in general, by means of wireless sensor networks provides convenience as needed to enable 'real-life' patient monitoring. While the benefits of wireless monitoring are significant, there remains the need to ensure sensitive patient information remains secure. For example, security is a mandatory requirement for such systems in order to both ensure patient safety and privacy and comply with legal requirements in healthcare such as HIPAA in the USA. Key management is fundamental to enable BSN security, since it provides and manages the cryptographic keys to enable further security services, such as authentication, confidentiality and integrity. Protection of the patient's privacy sphere is needed, in order to protect patients from tracking, and guarantee that only granted personal can access to patient's medical information.

A key distribution system used to distribute cryptographic keys to medical devices is know as the Hierarchical Deterministic Pairwise Key Pre-distribution Scheme (HDPKPS), which is described in cross-referenced application US 2009/0129599. The HDPKPS is a very efficient key distribution system that allows any pair of devices (chosen from a large pool of medical devices) to generate a pairwise key. Key generation is carried out by exploiting the HDPKPS keying material that each medical device stores. A pairwise key can be used to provide further security services, and be linked to the unique HDPKPS' identifier so that a device can be unambiguously authenticated.

Additionally, the HDPKPS keying material maps predefined relationships, such as ownership, via a hierarchical infrastructure of security domains enabling in this way precise device identification. For example, a device can be classified according to the ownership into a four level hierarchical security domains, namely manufacturer, health institution, hospital, and department.

The mapping of predefined relationships is carried out by distributing to each and every of the nodes a set of keying material (KM). The keying material a node carries is linked to the different security domains to which that node belongs. For instance, if a node belongs to a supplier, health institution A, hospital H, and department D, that node would get a set of KM composed of four independent sub-sets of KM, namely: $KM_{supplier}$, $KM_A$, $KM_H$, and $KM_D$. Each of these sub-sets of KM are linked to previous security domains.

In the HDPKPS, when two nodes want to agree on a common key, they exchange the HDPKPS identifiers that identify the SDs to which the nodes belong. With this information, both nodes can identify the origin of the other party in this hierarchical distribution of SDs, identify to each other and agree on a common key by exploiting the common keying material. For instance, given two nodes belonging to Philips, same health institution, same hospital, but different departments, both nodes can recognize the origin of the other node, and agree on a common pairwise key based on the keying material linked to the deepest common security domain (DCSD), namely, the hospital keying material. The common key is generated at this level, as it provides the maximum security level.

The keying material used to agree on a common key, can be based on a pre-distributed secret, a k-secure approach based on polynomials, or public keys. The HDPKPS uses a hierarchical distribution of 2-secure DPKPS keying material. This keying material is linked to each security domain, and two nodes belonging to the same SD get correlated but different sets of keying material.

Since future patient monitoring will enable patient's to move freely within of hospital's facilities, or even pervasive patient monitoring, high secure patient monitoring must be ensured wherever the patient is located.

There is a need of identifying different features of medical devices in an easy manner, without requiring heavy cryptography (e.g. public key) or access to a server. In a representative solution, a (medical) device or entity linked to a public key that authenticates that that device or entity is featured by set of identifiers can be substituted by discrete identifiers where identifiers are be arranged according to orthogonal features classified in a hierarchical manner, and each feature can be authenticated in an individual manner. Additionally, there is a need, for a method, apparatus and system that improves patient security in wireless patient monitoring systems.

In a representative embodiment, a method of security management in a wireless network comprises: identifying a plurality of orthogonal classifications of medical devices; generating identifiers for each security domain within each of the orthogonal classifications; generating keying material for each identifier; and exchanging identifiers to establish a key agreement, or an access control, or privacy protection or a combination thereof.

In another representative embodiment, a security system for a wireless network, includes: a wireless device; and a medium access controller (MAC) operative to: identify a plurality of orthogonal classifications of the wireless devices and to assign at least one of the orthogonal classifications to each wireless device and to generate identifiers for each security domain within each of the orthogonal classifications and to assign the identifiers to each wireless sensor and each wireless node, wherein the wireless devices exchange the identifiers to establish a key agreement, or an access control, or privacy protection or a combination thereof.

In accordance with yet another representative embodiment, a wireless device operative to communicate with other wireless devices in a network, comprises: an orthogonal classification; an identifier for each security domain within each orthogonal classification; and a keying material for each identifier wherein each wireless device is adapted to exchange one or more of respective identifiers to establish a key agreement, or an access control, or privacy protection or a combination thereof.

The present teachings are best understood from the following detailed description when read with the accompanying drawing figures. The features are not necessarily drawn to scale. Wherever practical, like reference numerals refer to like features.

Figure 1:
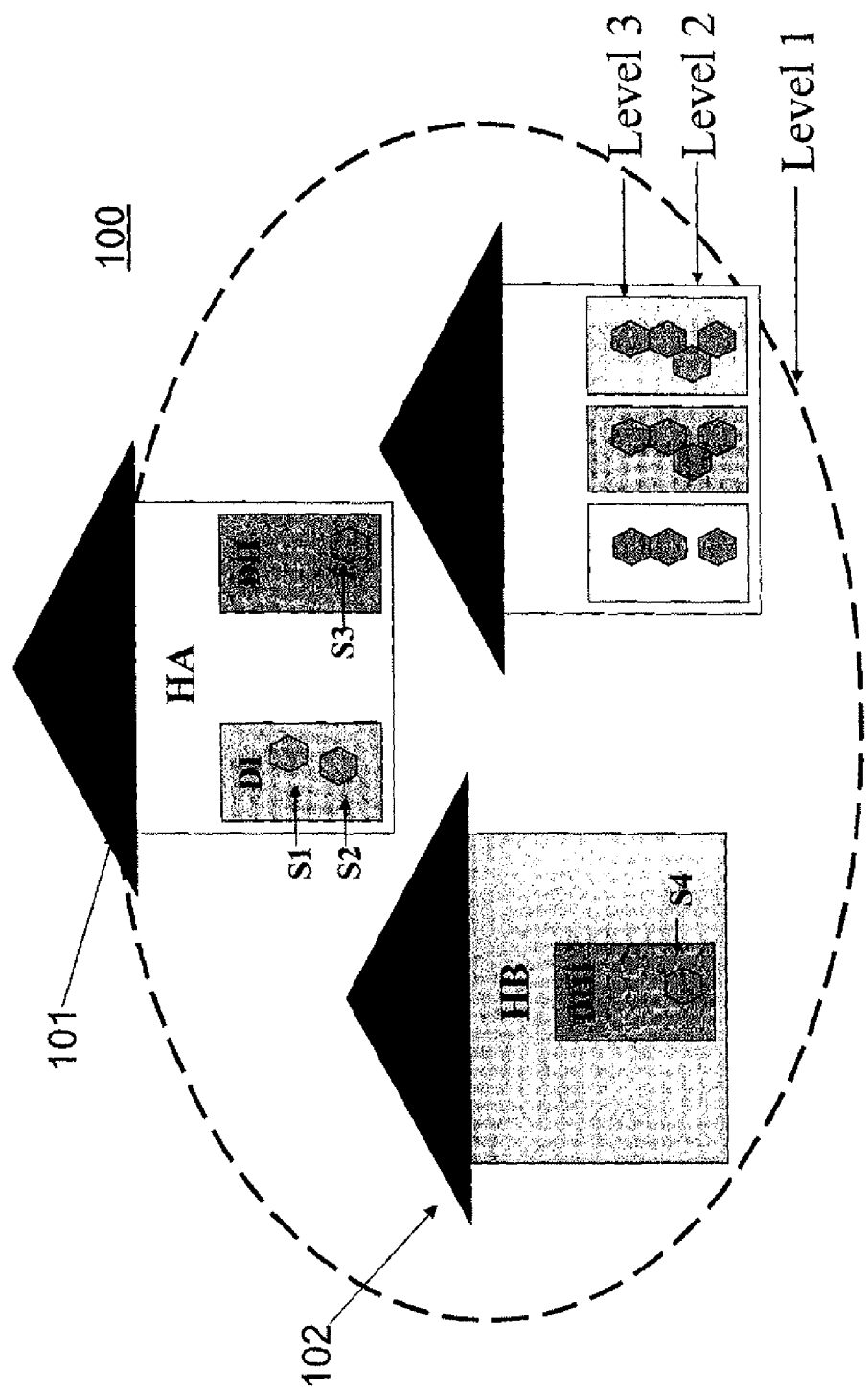
FIG. 1 is a conceptual schematic diagram of a wireless system in accordance with a representative embodiment.

As used herein, the terms 'a' or 'an', as used herein are defined as one or more than one.

In the following detailed description, for purposes of explanation and not limitation, illustrative embodiments disclosing specific details are set forth in order to provide a thorough understanding of the present teachings. Moreover, descriptions of well-known devices, hardware, software, firmware, methods and systems may be omitted so as to avoid obscuring the description of the illustrative embodiments. Nonetheless, such hardware, software, firmware, devices, methods and systems that are within the purview of one of ordinary skill in the art may be used in accordance with the illustrative embodiments. It is emphasized that while the representative embodiments are directed to medical sensors and monitors, medical wireless sensor networks, and ZigBee networks, the present teachings may be otherwise applied where authentication is desired before communications between devices occurs. For example, the present teachings may be applied to other types of monitoring/measuring systems, such as RFID systems, with suitable modifications.

The detailed description which follows presents methods that may be embodied by routines and symbolic representations of operations of data bits within a computer readable medium, associated processors, microprocessors, digital storage oscilloscopes, general purpose personal computers, manufacturing equipment, configured with data acquisition cards and the like. In general, a method herein is conceived to be a sequence of steps or actions leading to a desired result, and as such, encompasses such terms of art as "routine," "program," "objects," "functions," "subroutines," and "procedures."

The illustrative embodiments may be implemented in one or more of a variety of wireless systems, networks, devices and protocols within the purview of one of ordinary skill in the art and in future wireless systems. Many aspects of the current invention of the representative embodiments can implemented in either the medium access control (MAC) or application layer. For purposes of illustration and not limitation, the wireless system/network may be compliant to one or more of the following protocols: IEEE 802.11 and its progeny, including ad-hoc networks; IEEE 802.15 and its progeny; and IEEE 802.22, and IEEE 802.15.4 (commonly referred to as ZigBee). As the details of such systems are within the purview of one of ordinary skill in the art, such details and their particular application to the present teachings are not described in order to avoid obscuring the description of the representative embodiments.

The representative embodiments are described in connection with medical networks and devices. This is merely an illustrative application. Notably, the present teachings may be applied to other systems system can be used to enable and improve further security services including distributed access control, device or entity identification, privacy protection and secure roaming in wireless networks, such as ZigBee networks. Notably, distributed access control can be achieved by limiting access (rights) to only those devices or entities that possess authorized identifiers and that can prove it according to pre-defined rules.

Beneficially, in medical applications and other contemplated applications, entity or device identification is improved as an entity or device is identified not only by a single identifier, but also according to its features. In this manner, an entity or device can show the possession of individual identifiers linked to individual features making possible more specific identification of a device or entity without requiring a public key or access to a dedicated server. Moreover, privacy protection can be achieved by limiting the identification information disclosed when starting a communication.

FIG. 1 is a conceptual schematic diagram of a wireless medical system 100 in accordance with a representative embodiment. The system 100 includes a plurality of medical devices ($S_1, S_2, \ldots S_n$), which are wireless medical devices. The devices comprise, illustratively, wireless medical devices, such as physiological condition sensors and monitors, bedside monitors, controllable medication dosing devices and personal digital assistants (PDAs). The system 100 also includes a hierarchical classification of the devices based on the ownership of those devices. Accordingly, a wireless device ($S_j, S_2, \ldots S_n$) of the system 100 may be categorized according to three levels: manufacturer of the device; medical facility (e.g., hospital); and medical department to which the device belong. If two devices belong to the same category at the same level, we say that both devices belong to the same security domain (SD) at that level. For instance, in the present illustration, devices $S_1$ and $S_2$ belong to the same department and hospital at security domains levels 3 and 2, respectively. If two devices belong to the same SD, the HDPKPS allows both devices to authenticate each other, and generate a pairwise key which can be used to provide further security services. In general, if two devices belong to the same SD (i.e., they share a common feature, such as location, ownerships, etc) the HDPKPS distributes correlated (but different) keying material linked to that SD to those devices. Both devices can exploit their respective sets of keying material to agree on a common key on a real-time basis. As used herein, the term 'exploit' means modify the keying material that was distributed previously in order to calculate a common deepest security level. For instance, suppose two devices, device a and device b, carry two sets of keying material (KMa and KMb), where the KMa=f(a,y) and KMb=f(b,y) and f(x,y) is a symmetric polynomial in two variables x,y, i.e. $f(x,y)=f(y,x)$. Then, both nodes a and b can exchange their identifiers, namely a and b. Then, device a exploits its KMa by calculating f(a,y) in y=b. The result is f(a,b). Node b can also exploit its keying material getting the same result f(b,a). Further details of authentication by HDPKPS are provided in the parent application referenced above.

While HDPKPS enables full-device hierarchical identification and full interoperability according to the ownership of the devices, in some scenarios, authentication by this method may not provide enough security or flexibility. To illustrate this, consider a Health Institution having two hospitals, H_A 101 and H_B 102. Each hospital has a cardiology department, D_I and D_II, respectively. Suppose a patient, who is treated in H_A/D_I, must be moved to H_B/D_II in order to be treated by another specialist. When the patient arrives to H_B/D_II, the patients sensors (e.g., $S_1$) from H_A/D_I can establish a secure communication with the bedside monitor of H_B/D_II as the sensors and bedside monitors belong to the same health institution, and they can use this category, and their corresponding sub-set of correlated keying material linked to that feature (or security domain) to generate a pairwise key. However, the resiliency of HDPKPS at higher security domains is weaker, and it might not provide enough security level.

In accordance with representative embodiments, greater flexibility and security is realized with a key distribution system known as orthogonal HDKPS (OKPS). The OKPS distributes keying material according to a multidimensional identification of a device or entity. Stated differently, the system distributes keying material linked to an identifier to each device in such a way that that device can identify or authenticate each feature in an individual manner. These hierarchical classifications of features are orthogonal in the sense that the SDs, which each classification defines, do not fully overlap, but just partially. For instance, in a city, several hospitals may be from several health institutions, but only in some of them might be the same medical specialty.

As will become clearer as the present description continues, the present invention (or OKPS) is based on the used of several orthogonal categories or classifications of features. In a representative embodiment, OKPS is based on two or more orthogonal classifications for wireless devices. In addition to a feature such as the ownership of devices, the hierarchical classifications of features illustratively include, but are not limited to: I). Location of the device (for instance, wireless devices can be classified according to country—state and city (Germany/NRW/Aachen)); medical specialty (for instance, wireless devices can be classified according to a general specialty, sub-specialty (surgery, neurosurgery)); expected operational zone in the medical facility/hospital (For instance, operational zone 1 might cover the orthopedic and radiology's department, as well as the gym facilities. In the same manner, other operational zones can be defined within of the hospital facilities.)

Beneficially, once the classifications are determined according to the different features of an entity or device and keying material distributed to the different entities and devices, two devices can exchange their identifiers, and exploit the distributed keying material to achieve device authentication and key agreement.

Figure 2:
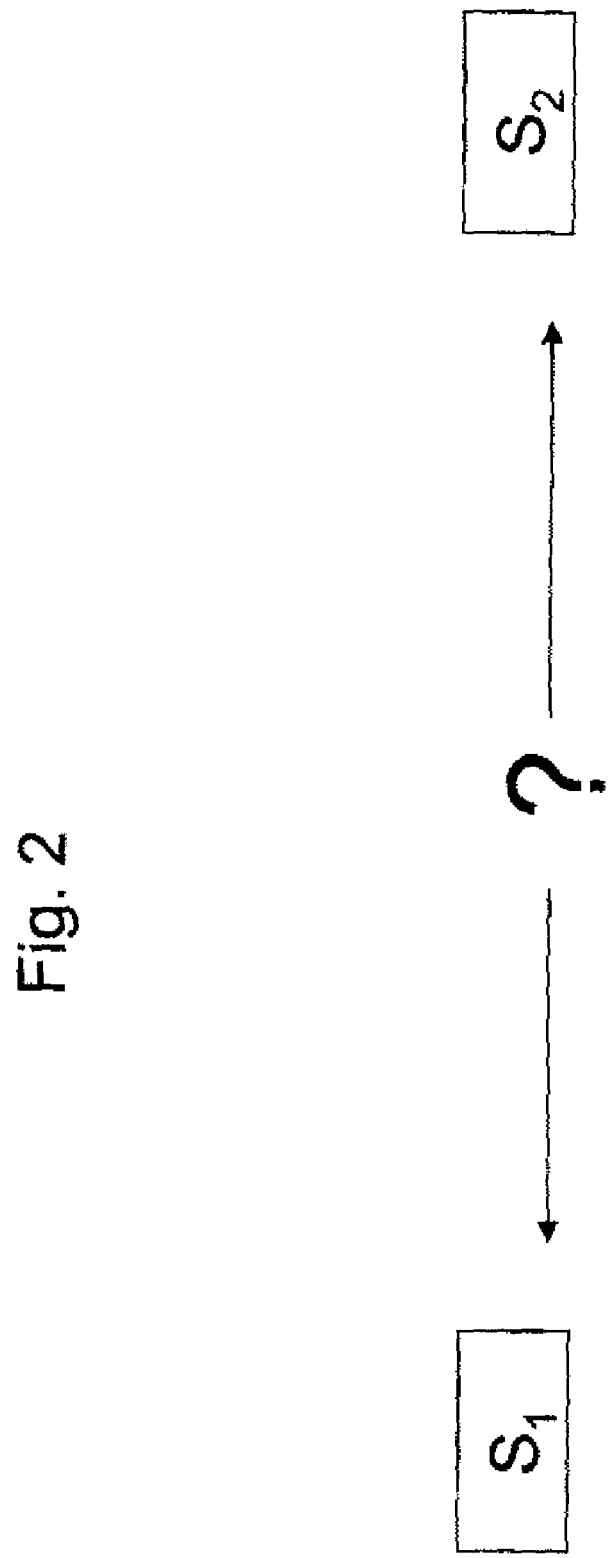
FIG. 2 is a conceptual schematic diagram of a wireless device seeking to communicate with another wireless device in accordance with a representative embodiment.
Figure 3:
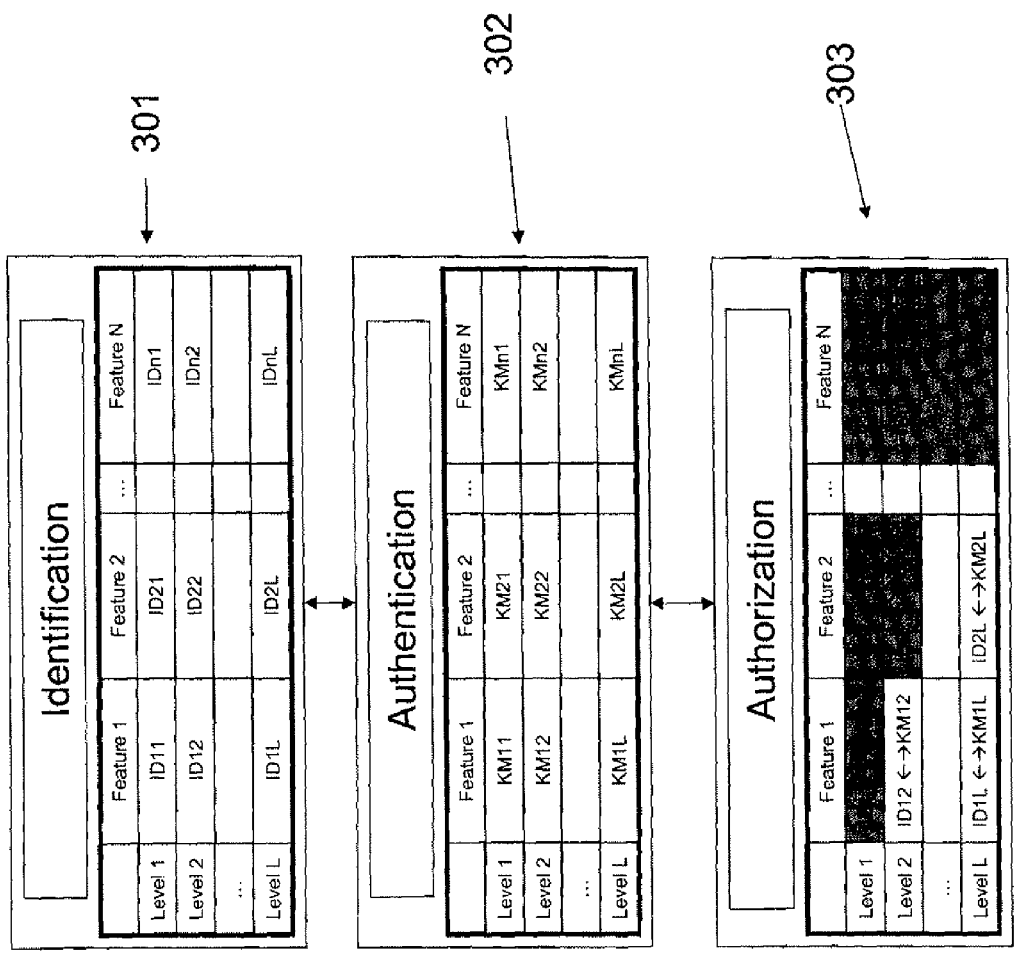
FIG. 3 shows tabular representations of classifications, identifiers and keying material of wireless devices in accordance with a representative embodiment.
Figure 4:
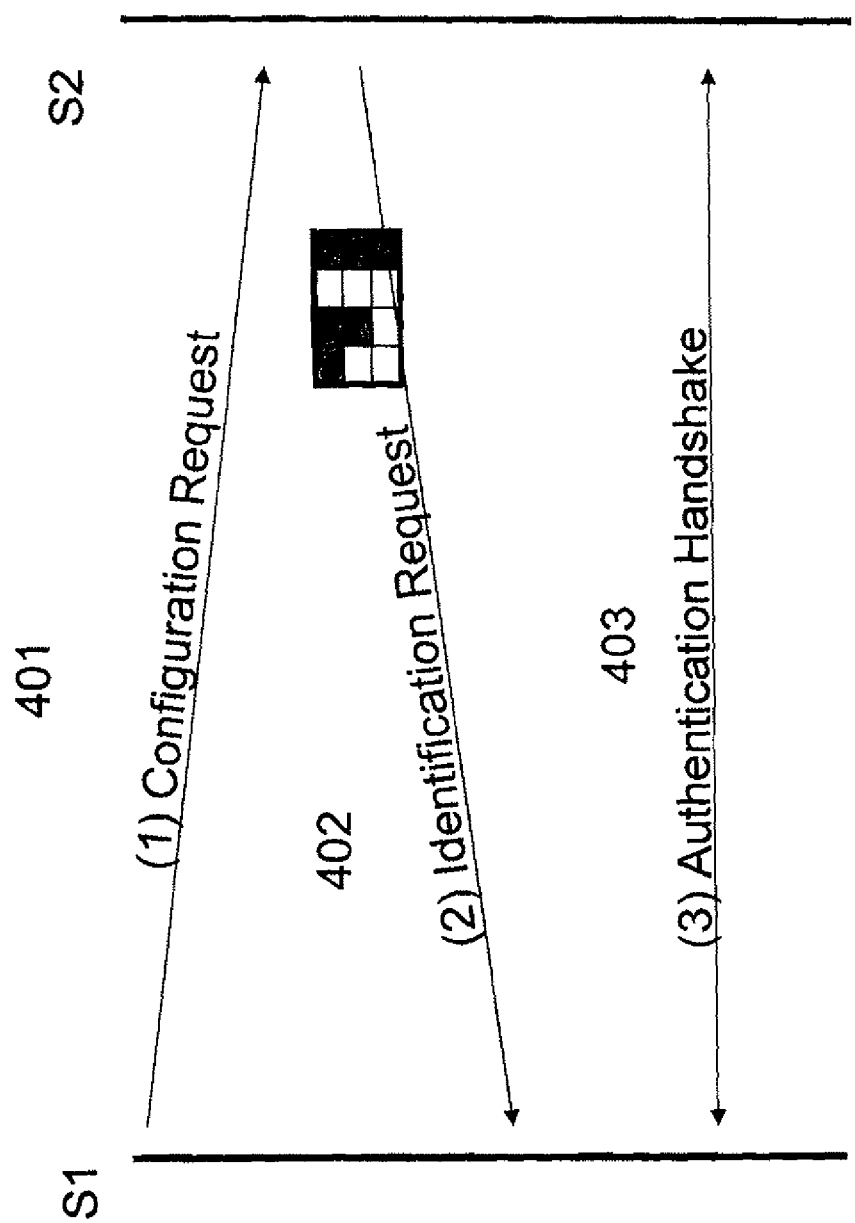
FIG. 4 is a conceptual schematic diagram of a sequence of establishing a secure connection at a deepest common security domain accordance with a representative embodiment.

FIGS. 2-4 disclose a method of effecting authentication between two wireless devices (e.g., $S_1$ and $S_2$) in accordance with a representative embodiment. For example, one of the wireless devices may be a patient's physiological sensor, and the other may be a clinician's PDA adapted to garner data from the sensor.

FIG. 2 is a conceptual schematic diagram of a wireless device $S_1$ seeking to communicate with another wireless device $S_2$. Each device includes at least two orthogonal classifications, security domains within the classification, identification and keying material.

For example,

TABLE 1

| Classification | SD | ID | Keying Material |
|---|---|---|---|
| Ownership | Philips | ID_o1 | KM_o1 |
| | Health Institution I | ID_o2 | KM_o2 |
| | Hospital A | ID_o3 | KM_o3 |
| | Department I | ID_o4 | KM_o4 |
| Location | Germany | ID_l1 | KM_l1 |
| | NRW | ID_l2 | KM_l2 |
| | Aachen | ID_l3 | KM_l3 |
| Medical Specialty | Surgery | ID_s1 | KM_s1 |
| | Brain's Surgery | ID_s2 | KM_s2 |
| Operational zone | Operational Zone 1 | ID_op1 | KM_op1 |

Continuing with the illustrative identifiers, when two devices $S_1$ and $S_2$ meet, the SD's identifiers are exchanged, allowing the devices to recognize ownership of the device, the location of that medical device, the medical specialty in which it is used, etc. This sequence is known as the identification sequence, and is illustrated in FIGS. 3 and 4.

In general, the identification sequence can be more complex in order to identify more complex roles of the devices and could be identify as a matrix. In that matrix, an axis identifies the different roles and the second axis assigns different values to the different roles at different depths in a hierarchical distribution. Table 1 can be seen as a specific example of such a matrix for previous example.

Initially, a configuration request 401 is sent from one wireless device to the other indicating the need for a secure connection. This is followed by an identification request 402 in which the requesting device sends a message including the minimum number of features to be disclosed for each feature (in order to enable privacy protection/distributed access control). These features are shown in table 301 and in general for feature f, the first $L_f$ identifiers must be disclosed, where Lf is the number of hierarchical levels in which the feature is organized. Notably, this step might be modified if both nodes use access control/privacy aware policies. In this case both nodes could exchange a sub-set of identifiers, in order to protect patient's privacy, or restrict access if the other party does not prove its memberships to a specific (and predefined) group, security domain, or feature. In general, after exchanging the identifiers, two devices look for the deepest common security domain for each and every of the features, i.e., the devices use the exchanged SD's identifiers to discover the DCSD for each independent HDPKPS. Both devices then generate a pairwise key K by combining each of the independent partial pairwise keys generated from each independent HDPKPS.

At step 403, the devices complete an authentication handshake. In this step, that takes place after exchanging the multidimensional identifiers shown in Table 302. For each identification feature i shown in Table 302, the devices identify the deepest common security domain j (*1). Next, the devices exploit their own pair {IDij-a, KMij-a} ($S_1$) and the IDij-b ($S_2$) to agree on a partial key Kij-ab. Next, the devices agree on a global secret K, for instance, by calculating the hash of all the partial pairwise keys K=h(K1j-ab||K2j-ab|| . . . ||Knj-ab) and make use of K to authenticate both nodes/enable secure communications. Accordingly, both devices make use of identifier and keying material associated with each of the DCSDs and at the deepest common SD to generate a partial pairwise key, Kp, as described by HDPKPS.

Figure 5:
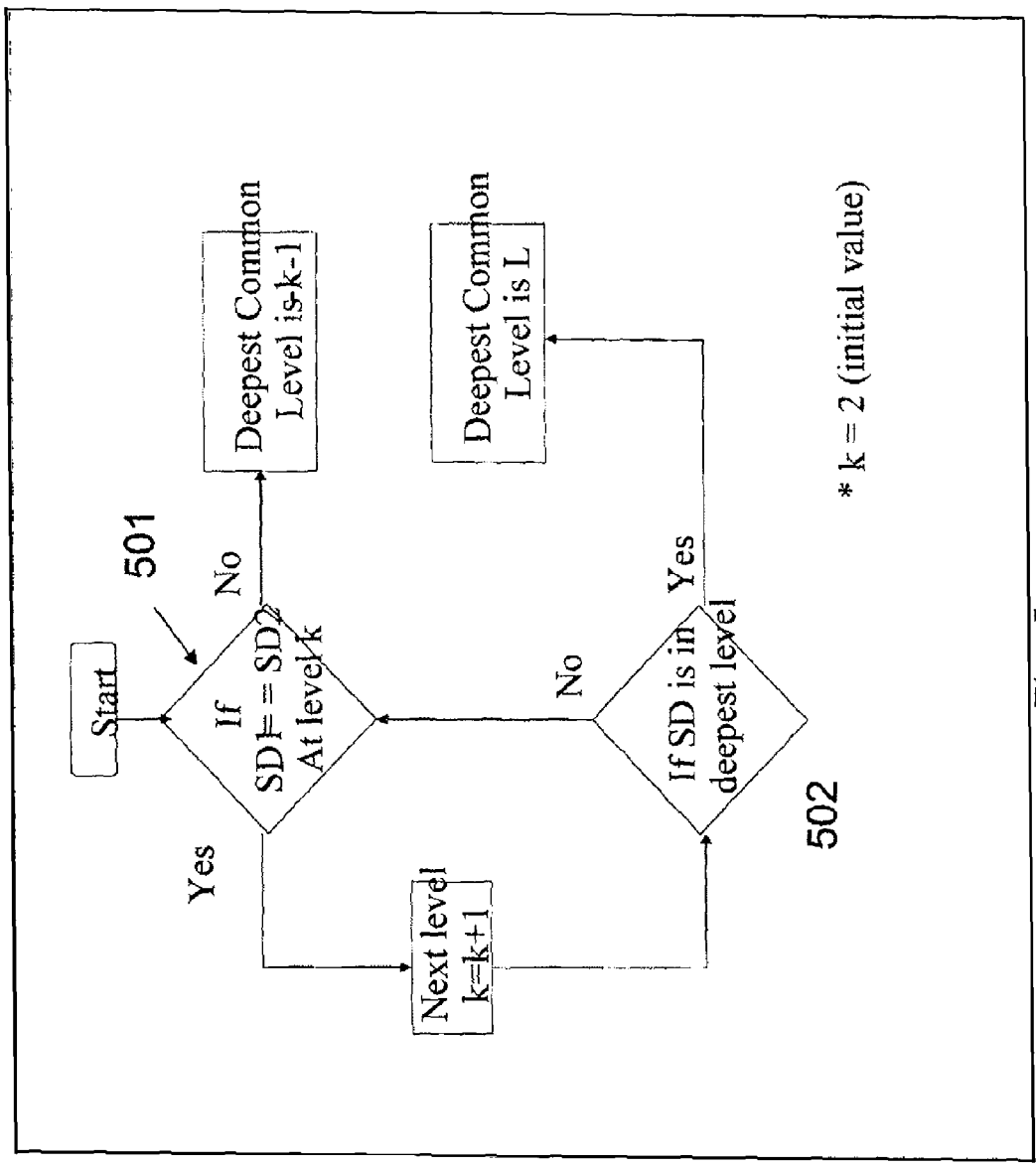
FIG. 5 is a flow-chart illustrating the search for the deepest common SD in accordance with a representative embodiment.

FIG. 5 is a flow-chart illustrating the search for the deepest common SD in accordance with a representative embodiment. The method relies on features and details described in connection with the embodiments previously described. Such details and features are not repeated in order to avoid obscuring the description of the presently described embodiments.

At step 501, during the authentication step, the wireless device determine whether they are in the same security domain (SD1=SD2). If not, then the lowest common level is k−1. If the devices are at the same SD, then they proceed to level k+1. At step 502, if the devices are not in the deepest SD, then the method reverts to step 501. If the devices are in the deepest SD, then the deepest level common level is L.

In general, the previous operation is repeated for each feature, so that two devices can identify the keying material they can use to agree on a common partial secret and to identify to each other for each and every of the features.

Certain examples illustrating the use and function of the methods, apparatuses and systems of the representative embodiments are provided. These examples are only illustrative and in no way limiting in nature.

The OKPS allows classifying a sensor node according to several features. This allows secure patient transfer from ICU to normal care unit. For example, consider a cardiac patient in a hospital who is operated due to a heart attack. During and the first few days after the operation he is attended at the ICU. However, after a couple of days he is transferred to a normal care unit specialized in cardiac patients, cardiac care unit (CCU). Wireless sensors used in this setting shall be configured according to an OKPS composed of two (hierarchical) security domains. On the one hand, these sensor nodes belong to the security domain of the ICU. Hence, these sensors shall carry keying material from the hospital and from the ICU's department. On the other hand, the operational zone of these sensors includes the CCU. Hence, those sensor nodes must also carry keying material of both orthogonal security domains.

A benefit of this implementation is that patients can keep the same sensor nodes during the whole treatment but with an optimal security level is higher as sensor nodes belong to two orthogonal security domains, namely ICU's keying material and CCU' keying material.

A cardiac patient in a hospital wears a wireless sensor node that continuously monitors his ECG. He has to go to the hospital's gym every day for exercising. During this period of time, patient A is monitored both at the cardiology department and gym. The OKPS allows this at a high security level, as cardiology and gym are in parallel supported as secure domains. Hence, the secure connection is not only based on the hospital level, but also in the operational zone of the sensor. This fact augments the resiliency of the system.

Additionally, the secure connection fosters transparent security roaming from one security domain to another. We can imagine that a medical network, such as a hospital medical network, is divided into several sub-wireless sensor network domains, or several ZigBee networks. Each ZigBee network controls its own security, but devices could keep keying material sets belonging to the different networks where a patient is to be treated. In this manner, when a patient moves from a zone A, with ZigBee network A, to other zone B, with ZigBee network B, the patient's sensor nodes already carry keying material linked to both zones, security domains, networks, or ZigBee networks, enabling transparent security roaming.

Protection of patient's privacy is of paramount importance for pervasive patient monitoring. For instance, if medical devices are identified by means of a unique identifier, patients could be tracked. The multi-dimensional OKPS' identifier helps preventing this problem by slightly modifying the operation mode of OKPS.

In the normal operation mode, a sensor would disclose all its identifiers. In the case of Table 1 a node would disclose:

TABLE 2

| SD | ID |
|---|---|
| Philips | ID_o1 |
| Health Institution I | ID_o2 |
| Hospital A | ID_o3 |
| Department I | ID_o4 |
| Germany | ID_l1 |
| NRW | ID_l2 |
| Aachen | ID_l3 |
| Surgery | ID_s1 |
| Brain's Surgery | ID_s2 |
| Operational Zone | ID_op1 |

In this additional privacy aware operation mode, a wireless sensor does not disclose all the identifiers, but only some of them. For instance:

TABLE 3

| SD | ID |
|---|---|
| Philips | ID_o1 |
| Health Institution I | ID_o2 |
| — | — |
| — | — |
| Germany | ID_l1 |
| NRW | ID_l2 |
| — | — |
| Surgery | ID_s1 |
| — | — |
| — | — |

Based on this information, a sensor node can still be identified but not completely, protecting in this manner patient's privacy. This represents a huge advantage when compared with other identification systems that require the disclosure of a single identifier linked to for instance the public key of the corresponding entity. Therefore, this system allows implementing privacy aware techniques in low-resource constrained devices.

Sensor nodes are identified by means of several orthogonal classifications. This enables a more precise authenticated identification, when required, of the ownership, location, illness, etc, of the patients. This can be very useful to detect for example medical errors during a patient transfer, as sensor nodes can identify the operation zone of the nodes. For instance, if a patient carries several sensor nodes with multi-dimensional identifiers, granted physicians can check whether that patient is located in the operation area, department, etc he should. In this manner, possible errors during patient transfer can be detected.

OKPS enables distributed access control features by making use of the orthogonal identification features of devices. For instance, the system could be configured in a way that only hospital devices fulfilling several features have access to patient's health information.

For instance, let us assume that patient's ECG sensor are preconfigured to enable patient monitoring of only bedside monitors that belong to the hospital in which a patient is treated or are in the same city and are linked to the cardiology specialty. In this case, patient's ECG sensor will only disclose patient's ECG vital signs to nodes that successfully authenticate as belonging to the same hospital, or to other hospital of the same city with the cardiology specialty.

In general, a minimum number of features can be required to perform specific actions. Hence, medical device or entity (e.g. a sensor node) could store a list with the features that are required to carry out those actions. Before an action is granted, the medical device requests the identification and authentication of a specific sub-set of features that is required to authorize the activity. If the other party can prove its identity, the action is granted, i.e., authorized. Otherwise, the action is rejected. This feature is useful particularly for new wireless sensor network standards such as ZigBee as access control is a compulsory requirement in new applications, and current centralized access control solutions have a limited scope and are not flexible enough.

In view of this disclosure it is noted that the various methods, apparatuses and systems described herein can be implemented in a variety of applications with variant devices, modalities, software and hardware. Moreover, applications other than patient monitoring may benefit from the present teachings. Further, the various devices, modalities, software and hardware and parameters are included by way of example only and not in any limiting sense. In view of this disclosure, those skilled in the art can implement the present teachings in determining their own applications and needed devices, software, hardware and other equipment to implement these applications, while remaining within the scope of the appended claims.

The invention claimed is:

1. A method of security management in a wireless network, the method comprising:
   identifying a plurality of orthogonal classifications of wireless medical devices;
   generating identifiers for each security domain within each of the orthogonal classifications;
   generating keying material for each identifier, the keying material including sets of at least one of Hierarchical Deterministic Pairwise Key Pre-distribution Scheme (HDPKPS) keying material and DPKPS keying material that identifies and authenticates orthogonal features of one of the wireless devices;
   exchanging identifiers to establish a key agreement, or an access control, or privacy protection or a combination thereof at the deepest common security domain within each orthogonal classification.

2. The method as claimed in claim 1, wherein the network is a medical network.

3. The method as claimed in claim 1, wherein the orthogonal classifications comprise: ownership, location, medical specialty and operational zone.

4. The method as claimed in claim 1, wherein the orthogonal classifications define security domains which do not fully overlap.

5. The method as claimed in claim 2, wherein at least one of the wireless medical devices is a wireless medical sensor.

6. The method as claimed in claim 5, wherein the wireless medical devices include: physiological condition monitors, controllable medication dosing devices and personal digital assistants (PDAs).

7. A security system for a wireless network, comprising:
   a plurality of wireless devices; and
   a medium access controller (MAC) operative to:
      identify a plurality of orthogonal classifications of the wireless devices,
      assign at least one of the orthogonal classifications to each wireless device,
      generate identifiers for each security domain within each of the orthogonal classifications,
      assign the identifiers to each wireless device,
      a key generator operative to generate keying material for each wireless device, the keying material including sets of at least one of Hierarchical Deterministic Pairwise Key Pre-distribution Scheme (HDPKPS) keying material and DPKPS keying material and identifying and authenticating orthogonal features of each wireless device,
   wherein the wireless devices exchange the identifiers to establish a key agreement, or an access control, or privacy protection or a combination thereof at a deepest common security domain within each orthogonal classification.

8. The security system as claimed in claim 7, wherein the key generator assigns the keying material to the wireless device, the keying material being linked to the identifiers that identify the wireless device.

9. The security system as claimed in claim 7, wherein the wireless device is a wireless medical sensor.

10. The security system as claimed in claim 9, wherein the wireless medical sensor and another wireless device are adapted to exchange respective identifiers to agree on a common keying material.

11. The system as claimed in claim 9, wherein the orthogonal classifications comprise: ownership, location, medical specialty and operational zone.

12. The system as claimed in claim 9, wherein the classification is based on ownership and comprises one or more of the following hierarchical security domains: a manufacturer; a medical facility; a department within the medical facility.

13. The system as claimed in claim 7, wherein the keying material of each security domain is independent of the keying material of the other security domains, so that the different features are identified and authenticated individually.

14. A security system for a wireless network which includes a plurality of wireless devices which communicate wirelessly, each wireless device operative to communicate with other wireless devices in a network, each wireless device carrying keying material for each of a plurality of identifiers for security domains and being configured to exchange one or more of the identifiers with another of the wireless devices to establish at least one of a key agreement, an access control, privacy protection or a combination thereof at a deepest common security domain within each orthogonal classification;
   wherein the security domains are defined by an orthogonal classification of the identifiers such that each wireless device carries keying material for orthogonal security domains which only partially overlap and do not fully overlap with the security domains of others of the wireless devices,
   wherein the keying material includes sets of at least one of Hierarchical Deterministic Pairwise Key Pre-distribution Scheme (HDPKPS) keying material and keying material that identifies and authenticates orthogonal features of one of the wireless devices.

15. The security system as claimed in claim 14, wherein the wireless devices are medical devices including: physiological condition monitors, controllable medication dosing devices and personal digital assistants (PDAs).

16. The security system as claimed in claim 14, wherein the orthogonal classifications comprise: ownership, location, medical specialty and operational zone.

17. The security system as claimed in claim 14, where the wireless device is a wireless medical device.

18. The security system as claimed in claim 14, wherein the wireless device is adapted to migrate or roam to among different orthogonal security domains.

* * * * *